US012151207B2

(12) United States Patent
Kambouris

(10) Patent No.: US 12,151,207 B2
(45) Date of Patent: *Nov. 26, 2024

(54) ISOTOPIC COMPOSITIONS II

(71) Applicant: BOTANICAL WATER TECHNOLOGIES IP LTD, London (GB)

(72) Inventor: Ambrosios Kambouris, Thurla (AU)

(73) Assignee: BOTANICAL WATER TECHNOLOGIES IP LTD, London (GB)

(*) Notice: Subject to any disclaimer, the term of this patent is extended or adjusted under 35 U.S.C. 154(b) by 411 days.

This patent is subject to a terminal disclaimer.

(21) Appl. No.: 16/959,307

(22) PCT Filed: Dec. 18, 2018

(86) PCT No.: PCT/AU2018/051349
§ 371 (c)(1),
(2) Date: Jun. 30, 2020

(87) PCT Pub. No.: WO2019/134014
PCT Pub. Date: Jul. 11, 2019

(65) Prior Publication Data
US 2020/0368686 A1   Nov. 26, 2020

(30) Foreign Application Priority Data
Jan. 2, 2018   (AU) ................................ 2018900005

(51) Int. Cl.
*B01D 59/04*  (2006.01)
*A23C 1/12*   (2006.01)
(Continued)

(52) U.S. Cl.
CPC ............. *B01D 59/04* (2013.01); *A23C 1/12* (2013.01); *A23L 2/08* (2013.01); *A23L 2/38* (2013.01);
(Continued)

(58) Field of Classification Search
CPC ........ B01D 59/04; B01D 59/08; B01D 59/26; B01D 61/002; B01D 61/027;
(Continued)

(56) References Cited

U.S. PATENT DOCUMENTS 5,855,921 A    1/1999  Somlyai
6,106,725 A *  8/2000  Hong ................... C02F 1/5236
                                           210/667
(Continued)

FOREIGN PATENT DOCUMENTS

EP    3329982 A1   6/2018
GB    1247590 A    9/1971
(Continued)

OTHER PUBLICATIONS

Dunbar, Oxygen and Hydrogen Isotopes in Fruit and Vegetable Juices (Year: 1983).*
(Continued)

*Primary Examiner* — Ekandra S. Miller-Cruz
(74) *Attorney, Agent, or Firm* — David D. Brush; Amanda M. Prose; Westman, Champlin & Koehler, P.A.

(57) ABSTRACT

Water-based compositions suitable for the hydration of a mammal, and particularly hydration of a human by oral or topical methods, and for industrial uses such as cooling, and the making of solutions and mixtures. A method for producing a beverage, an industrial process water, an industrial solvent, or topical dermatological composition includes: providing a water source, the water molecules having oxygen or hydrogen atoms of different isotopes, (i) fractionating
(Continued)

the water source to produce a fraction enriched in water molecules having an abundance of at least one of the oxygen or hydrogen isotopes being greater or less than the abundance found in the water source, or (ii) where the water source is already enriched in heavy water, fully or partially maintaining the level of enrichment.

5 Claims, 2 Drawing Sheets

(51) Int. Cl.
| | |
|---|---|
| A23L 2/08 | (2006.01) |
| A23L 2/38 | (2021.01) |
| B01D 59/08 | (2006.01) |
| B01D 59/26 | (2006.01) |
| B01D 61/00 | (2006.01) |
| B01D 61/02 | (2006.01) |
| B01D 61/14 | (2006.01) |
| B01D 61/58 | (2006.01) |
| B01D 69/12 | (2006.01) |
| C01B 5/02 | (2006.01) |
| C02F 1/04 | (2023.01) |

(52) U.S. Cl.
CPC ............ *B01D 59/08* (2013.01); *B01D 59/26* (2013.01); *B01D 61/002* (2013.01); *B01D 61/027* (2013.01); *B01D 61/149* (2022.08); *B01D 61/58* (2013.01); *B01D 69/1216* (2022.08); *C01B 5/02* (2013.01); *C02F 1/04* (2013.01)

(58) Field of Classification Search
CPC .... B01D 61/146; B01D 61/58; B01D 61/025; B01D 61/145; B01D 2325/42; B01D 69/02; B01D 69/12; B01D 59/10; B01D 59/14; B01D 59/50; A23C 1/12; A23L 2/08; A23L 2/38; A23L 2/72; C01B 5/02; C02F 1/04; C02F 1/283; C02F 1/442; C02F 1/22; C02F 1/441; C02F 1/444; C02F 1/445; C02F 1/68; C02F 2103/023; C02F 2103/026; C02F 1/28; C02F 2103/20; C02F 2103/26; C02F 2103/32; C02F 2303/00; A61K 2800/805; A61K 8/19; A61K 8/9789; A61K 8/9794; A61Q 19/00; A61Q 19/08; A23V 2002/00
USPC .......................................................... 203/5
See application file for complete search history.

(56) References Cited

U.S. PATENT DOCUMENTS

| | | | |
|---|---|---|---|
| 6,348,153 B1 | 2/2002 | Patterson et al. | |
| 6,984,327 B1 | 1/2006 | Patterson | |
| 9,475,007 B2* | 10/2016 | Wilson .................... | B32B 37/24 |
| 11,673,071 B2* | 6/2023 | Kambouris ............... | A23L 2/38 |
| | | | 424/613 |
| 2003/0141177 A1 | 7/2003 | Countz | |
| 2009/0008235 A1 | 1/2009 | Goel et al. | |
| 2012/0255899 A1* | 10/2012 | Choi ..................... | B01D 69/106 |
| | | | 977/734 |
| 2015/0209734 A1* | 7/2015 | Chiu ........................ | C02F 1/44 |
| | | | 210/489 |
| 2015/0217231 A1 | 8/2015 | Kambe et al. | |
| 2017/0016664 A1* | 1/2017 | Leavitt ...................... | F25D 5/02 |
| 2018/0311617 A1 | 11/2018 | Selivanenko et al. | |

FOREIGN PATENT DOCUMENTS

| | | | | |
|---|---|---|---|---|
| JP | S-6214928 A | * | 7/1985 | ............. B01D 59/04 |
| JP | 2008529491 A | | 8/2008 | |
| JP | 2008529492 A | | 8/2008 | |
| JP | 2016532552 A | | 10/2016 | |
| RU | 2270590 C1 | | 2/2006 | |
| RU | 2287318 C2 | | 11/2006 | |
| WO | 9308794 A1 | | 5/1993 | |
| WO | 2005070438 A1 | | 8/2005 | |
| WO | 2006028400 A1 | | 3/2006 | |
| WO | 2006085784 A1 | | 8/2006 | |
| WO | 2006085785 A1 | | 8/2006 | |
| WO | 2008136701 A1 | | 11/2008 | |
| WO | 2010083574 A1 | | 7/2010 | |
| WO | 2013096996 A1 | | 7/2013 | |
| WO | 2017001874 A1 | | 1/2017 | |
| WO | 2017017433 A2 | | 2/2017 | |
| WO | 2017065647 A1 | | 4/2017 | |
| WO | 2018053578 A1 | | 3/2018 | |

OTHER PUBLICATIONS

Yang, Ultrathin graphene-based membrane with precise molecular sieving and ultrafast solvent permeation (Year: 2017).*
Prasad, B. et al., "Enrichment of H217O from Tap Water, Characterization of the Enriched Water, and Properties of Several 17O-Labeled Compounds" Anal. Chem. 2011, vol. 83, pp. 231-239; Abstract, Experimental section; Conclusions; table 1.
Yunianta, B-L. Z. et al., " Stable isotope fractionation in fruit juice concentrates: Application to the authentication of grape and orange products" J Agric. Food Chem 1995, vol. 43 pp. 2411-2417; Abstract; section 3: materials and methods: Table 1; Conclusion.
Dunbar, J et al., "Oxygen and Hydrogen isotopes in fruit and vegetable juices" Plant Physiol. 1983, vol. 72, pp. 725-727; Abstract ; p. 725, left hand column, lines 1-12; Results; Discussion.
Kim.K.et al,. "Isotopic enrichment of liquid water during evaporation from water surfaces" , Journal Hydrology, 2011, vol. 399, 364-375 Figure 1; table 2; Section 6. Conclusions.
International Search Report dated Feb. 27, 2018 for corresponding International Patent Application PCT/AU2018/051349 filed on Dec. 18, 2018.
Written Opinion of the International Searching Authority dated Feb. 27, 2018 for corresponding International Patent Application PCT/AU2018/051349 filed on Dec. 18, 2018.
Kiyosawa, K. "Freezing Point of Mixtures of H 16 2 O with H 17 2 O and Those of Aqueous CD 3 CH 2 OH and CH 13 3 CH 2 OH Solutions", Journal of Solution Chemistry, (Apr. 1, 2004), vol. 33, No. 4, pp. 323-328, XP055498954 [A] 1-15.
Office Action issued for BR patent application Serial No. BR112020013545-3, dated Jun. 8, 2022.
Office Action issued for EP patent application Serial No. 18898725. 9, dated Jan. 18, 2022.
International Search Report issued for PCT/AU2018/051349, dated Feb. 27, 2019.
Office Action issued for JP patent application Serial No. 2020-555268, dated Nov. 1, 2011, with English machine translation.
Office Action issued for RU patent application Serial No. 2020125477/05(044287), dated Aug. 4, 2022, with English machine translation.
Search Report issued for RU patent application Serial No. 2020125477/05(044287), dated Jul. 27, 2022, with English 7 machine translation.

\* cited by examiner

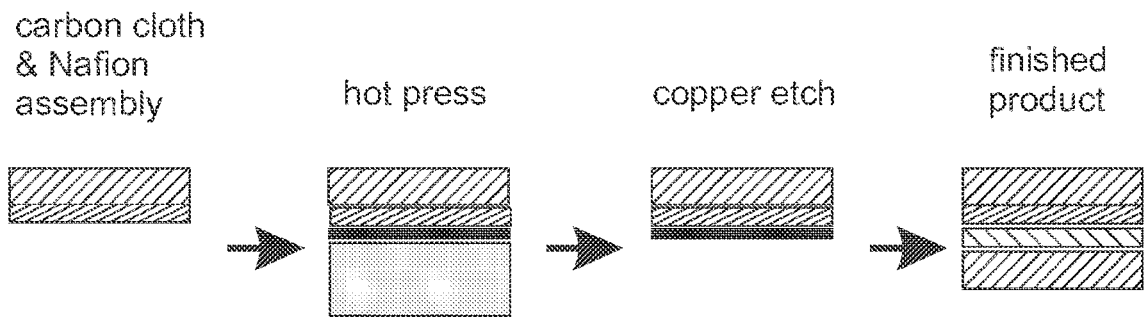
FIG. 2A
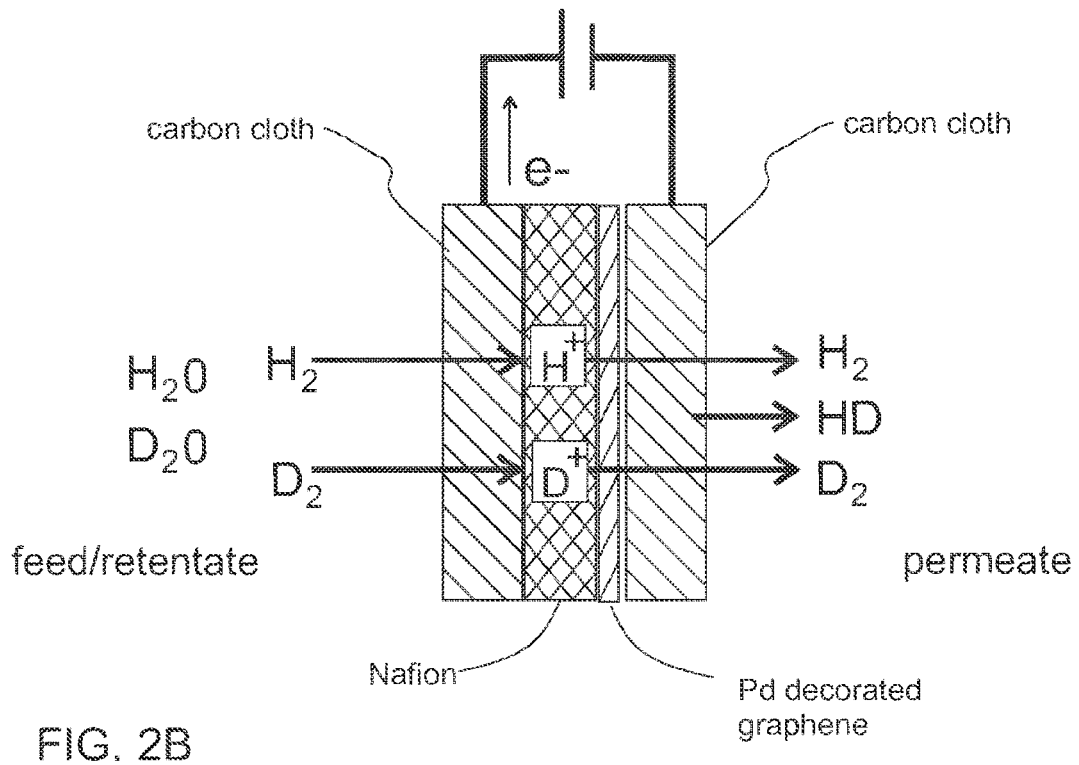
FIG. 2B
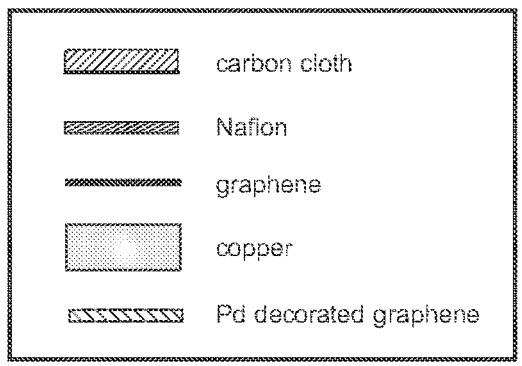

ISOTOPIC COMPOSITIONS II

The present application is a Section 371 National Stage Application of International Application No. PCT/AU2018/051349, filed Dec. 18, 2018 and published as WO 2019/134014 A1 on Jul. 11, 2019, in English, which claims priority from Australian provisional patent application 2018900005, filed Jan. 2, 2018, the contents of which are hereby incorporated by reference in their entireties.

FIELD OF THE INVENTION

The present invention relates to the field of water-based compositions suitable for the hydration of a mammal, and particularly hydration of a human by oral or topical means. The present invention further relates to the field of water for industrial uses such as cooling.

BACKGROUND TO THE INVENTION

Water is a ubiquitous biological solvent, without which life cannot survive. Humans are particularly vulnerable to dehydration given that body temperature is modulated at least in part by sweating. While sweating is important for body temperature regulation it can also be a major source of water and solute loss. Maximum rate of sweating is up to 50 mls/min or 2,000 mls/hr in the acclimatised adult. This rate cannot be sustained, however losses up to 25% of total body water are possible under severe stress.

The prior art provides many different types of beverages formulated so as to replace water and electrolytes lost by way of sweating. Such beverages are typically consumed at or around a time of physical exertion. While generally effective, these beverages do not alter the amount of heat that can be carried away from the body given the fixed latent heat of evaporation of water.

Quite apart from the biological need for water, hydration in humans is also important for the skin having regard to function and aesthetic considerations. Under conditions of dehydration, the upper layers of the skin can become cracked, thereby creating a portal for the entry of infective agents. Dehydrated skin can also become irritated, leading to inflammatory responses that can lead to flushing and swelling of the skin. Furthermore, pathological conditions such as psoriasis can be exacerbated by dehydration of the skin.

With regard to aesthetic considerations, dehydrated skin loses plumpness and can take on a flaccid appearance. Any wrinkling of the skin appears more prominent, and the skin loses shine. A person having dehydrated skin often appears old or unhealthy.

In addressing aesthetic problems associated with skin dehydration, the prior art provides a vast range of hydrating topical compositions such as creams, gels lotions and the like which aim to infuse water molecules into the upper layers of skin. While generally effective in the short term, the rapid evaporation of water from the skin means that the skin soon returns to a state of lower hydration. These topical compositions may further comprise oils and other substances which aim to form a layer on the skin so as to limit water loss. However, the oils and other substances can act to block pores and congeal with makeup foundation and cosmetic facial powders.

Water is also essential for many industrial processes such as cooling, the production of steam, cleaning and rinsing receptacles and conduits and the like. It is a problem is that the rate of evaporation of water industrial process water can be slow or too rapid, or require significant amounts of energy and particularly heat energy.

Water is also used as a solvent in many industrial process. A problem in this area is obtaining the required water and at a sufficient level of purity for the required use.

It is an aspect of the present invention to overcome or ameliorate a problem of the prior art by providing improved beverages and topical compositions for the hydration of a mammal, and particularly a human. It is a further aspect to provide an alternative to prior art beverages and topical compositions.

The discussion of documents, acts, materials, devices, articles and the like is included in this specification solely for the purpose of providing a context for the present invention. It is not suggested or represented that any or all of these matters formed part of the prior art base or were common general knowledge in the field relevant to the present invention as it existed before the priority date of each claim of this application.

SUMMARY OF THE INVENTION

In a first aspect, but not necessarily the broadest aspect, the present invention provides a beverage comprising water molecules, the water molecules having oxygen or hydrogen atoms of different isotopes, the beverage being enriched in at least one of the oxygen or hydrogen isotopes, the enrichment being in reference to (i) the amount of that oxygen or hydrogen isotope in the water used to produce the beverage or (ii) the amount of that oxygen or hydrogen isotope in ground water, or (iii) Vienna Standard Mean Ocean Water.

In one embodiment of the beverage, the abundance of at least one isotope is:
for isotope 16O: 0.99757 mole fraction,
for isotope 17O: $3.8 \times 10^{-4}$ mole fraction, or
for isotope 18O: $2.05 \times 10^{-3}$ mole fraction In one embodiment of the beverage, the abundance of the at least one isotope is defined by the range:
for isotope 16O: 0.99738 to 0.99776 mole fraction,
for isotope 17O: $3.7 \times 10^{-4}$ to $4.0 \times 10^{-4}$ mole fraction, or
for isotope 18O: $1.88 \times 10^{-3}$ to $2.22 \times 10^{-3}$ mole fraction In one embodiment of the beverage, the abundance of the 17O isotope is less than $3.8 \times 10^{-4}$ mole fraction, and/or the abundance of the 18O isotope is less than $2.05 \times 10^{-3}$ mole fraction, and/or the abundance of the 16O isotope is greater than about 0.99757 mole fraction.

In one embodiment of the beverage, the abundance of the 17O isotope is less than $3.7 \times 10^{-4}$ mole fraction, and/or the abundance of the 18O isotope is less than $2.22 \times 10^{-3}$ mole fraction, and/or the abundance of the 16O isotope is greater than about 0.99776 mole fraction.

In one embodiment of the beverage, the delta-O-18 of the water molecules is greater than or less than about 0 0/00. In one embodiment of the beverage, the delta-O-18 of the water molecules is greater than about 5, 10, 15, 20, 25, 30, 35, 40, 45, 50, 55, 60, 65, 70, 75, 80, 85, 90, 95 or 100 0/00. In one embodiment of the beverage, the delta-O-18 of the water molecules is less than about −5, −10, −15, −20, −25, −30, −35, −40, −45, −50, −55, −60, −65, −70, −75, −80, −85, −90, −95 or −100 0/00.

In addition or as an alternative to enrichment in respect of oxygen molecules, heavy water may be generated by enriching for water molecules having two deuterium atoms (having nucleus with a neutron and a proton) in place of the two protium atoms (having a nucleus with a proton only) of ordinary water. As discussed more fully herein infra, it is proposed that molecular sieves (including graphene, graphene oxide, and boron nitride molecular sieves) may be used to separate water having different hydrogen isotopes and/or different oxygen isotopes. As will be appreciated the weight of a heavy water molecule, however, is not substantially different from that of a normal water molecule, because about 89% of the molecular weight of water comes from the single oxygen atom rather than the two hydrogen atoms. The colloquial term heavy water refers to a highly enriched water mixture that contains mostly deuterium oxide $D_2O$, but also some hydrogen-deuterium oxide (HDO) and a smaller number of ordinary hydrogen oxide $H_2O$ molecules. For instance, a heavy water may be up to 99.75% enriched by hydrogen atom-fraction. This means that 99.75% of the hydrogen atoms are of the heavy type. For comparison, ordinary water (the "ordinary water" used for a deuterium standard) contains only about 156 deuterium atoms per million hydrogen atoms, meaning that 0.0156% of the hydrogen atoms are of the heavy type.

Heavy water is not radioactive. In its pure form, it has a density about 11% greater than water, but is otherwise physically and chemically similar. Nevertheless, the various differences in deuterium-containing water (especially affecting the biological properties) are larger than in any other commonly occurring isotope-substituted compound because deuterium is unique among heavy stable isotopes in being twice as heavy as the lightest isotope. This difference increases the strength of water's hydrogen-oxygen bonds, and this in turn is enough to cause differences that are important to some chemical reactions.

In one embodiment of the beverage, the water molecules are derived from a water source, and the abundance of at least one of the oxygen or hydrogen isotopes being greater or less than the abundance of the at least one of the oxygen or hydrogen isotopes in the water source.

In one embodiment of the beverage, the water source is a tissue of a plant, or a dairy material, or drawn from a natural body of water. In one embodiment of the beverage, the plant tissue is a reproductive or a vegetative tissue. In one embodiment of the beverage, the plant tissue is a fruit, a vegetable, a seed, a leaf, a stalk, or a root. The water source may also be a sap or a tree water of a plant.

In one embodiment of the beverage, the beverage comprises a food grade additive.

In one embodiment of the beverage, the additive is a colouring agent, a flavouring agent, an electrolyte, a sweetener, a preservative, a dissolved or undissolved gas, a nutrient, a vitamin, a pharmaceutical agent, a probiotic, or a prebiotic.

In another aspect, the invention provides a food grade vessel comprising the beverage as described herein.

In one embodiment, the vessel comprises a food grade lid forming a hermetic seal with the vessel.

In one aspect, the present invention provides an item used in an industrial process in contact with the industrial process water as described herein.

In another aspect, the present invention provides a process intermediate or product of an industrial process comprising the industrial solvent as described herein.

In a further aspect, the present invention provides a topical dermatological composition comprising water molecules, the water molecules having oxygen or hydrogen atoms of different isotopes, the beverage being enriched in at least one of the oxygen or hydrogen isotopes, the enrichment being in reference to (i) the amount of that oxygen or hydrogen isotope in the water used to produce the beverage or (ii) the amount of that oxygen or hydrogen isotope in ground water, or (iii) Vienna Standard Mean Ocean Water.

In one embodiment of the composition, the abundance of the at least one isotope is:
for isotope 16O: 0.99757 mole fraction,
for isotope 17O: 3.8×10−4 mole fraction, or
for isotope 18O: 2.05×10−3 mole fraction In one embodiment of the composition, the abundance of the at least one isotope is defined by the range:
for isotope 16O: 0.99738 to 0.99776 mole fraction,
for isotope 17O: 3.7×10−4 to 4.0×10−4 mole fraction, or
for isotope 18O: 1.88×10−3 to 2.22×10−3 mole fraction In one embodiment of the composition, the abundance of the 17O isotope is greater than 3.8×10−4 mole fraction, and/or the abundance of the 18O isotope is greater than 2.05×10−3 mole fraction, and/or the abundance of the 16O isotope is less than about 0.99757 mole fraction.

In one embodiment of the composition, the abundance of the 17O isotope is greater than 4.0×10−4 mole fraction, and/or the abundance of the 18O isotope is greater than 2.22×10−3 mole fraction, and/or the abundance of the 16O isotope is less than about 0.99738 mole fraction.

In one embodiment of the composition, the delta-O-18 of the water molecules is greater than or less than about 0 0/00. In one embodiment of the composition, the delta-O-18 of the water molecules is greater than about 5, 10, 15, 20, 25, 30, 35, 40, 45, 50, 55, 60, 65, 70, 75, 80, 85, 90, 95 or 100 0/00. In one embodiment of the composition, the delta-O-18 of the water molecules is less than about −5, −10, −15, −20, −25, −30, −35, −40, −45, −50, −55, −60, −65, −70, −75, −80, −85, −90, −95 or −100 0/00.

In one embodiment of the composition, the water molecules are derived from a water source, and the abundance of at least one of the oxygen or hydrogen isotopes being greater or less than the abundance of the at least one of the oxygen or hydrogen isotopes in the water source.

In one embodiment of the composition, the water source is a tissue of a plant, or a dairy material, or drawn from a natural body of water. In one embodiment of the composition, the plant tissue is a reproductive or a vegetative tissue. In one embodiment of the composition, the plant tissue is a fruit, a vegetable, a seed, a leaf, a stalk, or a root. The water source may also be a sap or a tree water of a plant.

In one embodiment the composition comprises a dermatologically acceptable additive. In one embodiment of the composition, the additive is hypoallergenic.

In one embodiment of the composition, the additive is a colouring agent, a perfume, a salt, a buffer, a preservative, an emulsifier, an oil, a vitamin, a detergent, a dermatologically active agent, or a pharmaceutical agent.

In a further aspect the present invention provides a cosmetic grade vessel comprising the composition as described herein. In one embodiment, the vessel comprises a cosmetic grade lid forming a hermetic seal with the vessel.

In yet a further aspect, the present invention provides a method for producing a beverage or a topical dermatological composition, the method comprising the steps of: providing a water source, the water molecules having oxygen or hydrogen atoms of different isotopes, (i) fractionating the water source to produce a fraction enriched in water molecules having an abundance of at least one of the oxygen or hydrogen isotopes being greater or less than the abundance found in the water source, or (ii) where the water source is already enriched in heavy water, fully or partially maintaining the level of enrichment.

In one embodiment of the method, the step of fractionating comprises the step of evaporating the water source.

In one embodiment of the method, the step of fractioning comprises the step of concentration or molecular sieving of the water source.

In one embodiment of the method, the water source is a tissue of a plant, or a dairy material, or drawn from a natural body of water. In one embodiment of the method, the plant tissue is a reproductive or a vegetative tissue. In one embodiment of the method, the plant tissue is a fruit, a vegetable, a seed, a leaf, a stalk, or a root. The water source may also be a sap or a tree water of a plant.

In one embodiment of the method, the plant tissue is treated to form a plant tissue extract, the plant tissue extract being subject of step fractionation step. In one embodiment of the method, the plant tissue extract is substantially a liquid. In one embodiment of the method, the liquid is a juice. In one embodiment of the method, the fractionation step is carried out using a food concentrator/evaporator.

In one embodiment of the method, the fractionation step comprises an evaporation step and a condensation step. In one embodiment of the method, the evaporation step is carried out until at least about 90, 91, 92, 93, 94, 95, 96, 97, 98, or 99% of water in the water source is evaporated. In one embodiment of the method, the condensate is differentially collected.

In one embodiment of the method, the evaporation step and the condensation step are carried out using a multiple-effect evaporator. For example, a juice may be evaporated to the desired level of concentration using an evaporator that has a series of effects. Each effect will remove water from the juice and each subsequent effect will evaporate water from juice that has altered oxygen or hydrogen isotope composition. Effectively, the condensate removed by each effect will differ in oxygen or hydrogen isotope composition. It has been shown that water from the first effect has a higher ratio of $H_2O^{16}/H_2O^{18}$ than water from the effect towards the end of the multi-effect evaporator.

In one embodiment of the method, the fractionation step comprises a freezing step.

In one embodiment of the method, the fractionation step is carried out until at least about 90, 91, 92, 93, 94, 95, 96, 97, 98, or 99% of water in the water source is frozen.

In one embodiment, the method comprises the step of contacting the water source, or a material derived from the water source with a molecular sieve.

In one embodiment, the molecular sieve is configured to discern between water molecules having differing isotopic compositions.

In one embodiment, the molecular sieve is configured to substantially remove a salt.

In one embodiment, the method comprises a forward osmosis step having a draw solution, and the method comprises the step of contacting the draw solution with a molecular sieve so as to regenerate the draw solution.

In one embodiment, the method comprises the step of a purification step selected from reverse osmosis, forward osmosis, activated carbon treatment, ultrafiltration, nanofiltration, and preparative chromatography.

In one embodiment of the method, the unfrozen water is differentially collected.

In one embodiment of the method, the fraction step is configured to provide a first fraction and a second fraction, the abundance of at least one of the oxygen or hydrogen isotopes being greater than the abundance found in the water source in the first fraction, and the abundance of at least one of the oxygen or hydrogen isotopes being less than the abundance found in the water source in the second fraction.

In one embodiment of the method, the method is for producing a beverage, the method comprises the step of adding a food grade additive to the first or second fraction.

In one embodiment of the method, the additive is a colouring agent, a flavouring agent, an electrolyte, a sweetener, a preservative, a dissolved or undissolved gas, a nutrient, a vitamin, a pharmaceutical agent, a probiotic, or a prebiotic.

In one embodiment the method comprises the step of transferring the first or second fraction to a food grade vessel.

In one embodiment the method comprises the step of hermetically sealing the vessel.

In one embodiment of the method, where the method is for producing a topical dermatological composition, the method comprises the step of adding a dermatologically acceptable additive to the first or second fraction.

In one embodiment of the method for producing a topical dermatological composition, the additive is a colouring agent, a perfume, a salt, a buffer, a preservative, an emulsifier, an oil, a vitamin, a detergent, a dermatologically active agent, or a pharmaceutical agent.

In one embodiment of the method for producing a topical dermatological composition, the method comprises the step of transferring the first or second fraction to a cosmetic grade vessel.

In one embodiment of the method for producing a topical dermatological composition, the method comprises the step of hermetically sealing the vessel.

In one embodiment, where the method is for producing an industrial process water, the method comprises the step of conveying the industrial process water so produced to a storage vessel.

In one embodiment, where the method is for producing an industrial process solvent, the method comprises the step of adding the industrial process solvent to a solute, or to a solution.

In some embodiments, the water source or a precursor of the water source, or an intermediate product is concentrated or fractionated by a method selected from the group consisting of a nanofiltration, reverse osmosis, forward osmosis, membrane distillation, or a methodology operating on the same or similar principle as any of the aforementioned methods.

Yet a further aspect of the present invention provides a method of treating or preventing dehydration or elevated temperature in a subject, the method comprising the step of administering to a subject in need thereof an effective amount of the beverage as described herein.

In one embodiment of the method of treatment, the elevated temperature is caused by physical activity or fever.

Yet a further aspect of the present invention comprises a method of treating or preventing dehydration or an aesthetic disorder of the skin of a subject, the method comprising the step of applying directly to the skin of a subject in need thereof an effective amount of the topical dermatological composition as described herein.

In one embodiment of the skin treatment method, the aesthetic disorder of the skin is skin laxity, wrinkles, skin flaking, skin dullness, or aged appearance.

BRIEF DESCRIPTION OF THE FIGURE

FIG. 2A is a highly diagrammatic representation of the steps involved in the fabrication of graphene/Nafion composite membrane.

FIG. 2B is a highly diagrammatic representation of the composite membrane of FIG. 2A for isotope separation by electrochemical pumping.

DETAILED DESCRIPTION OF THE PRESENT INVENTION

Figure 1:
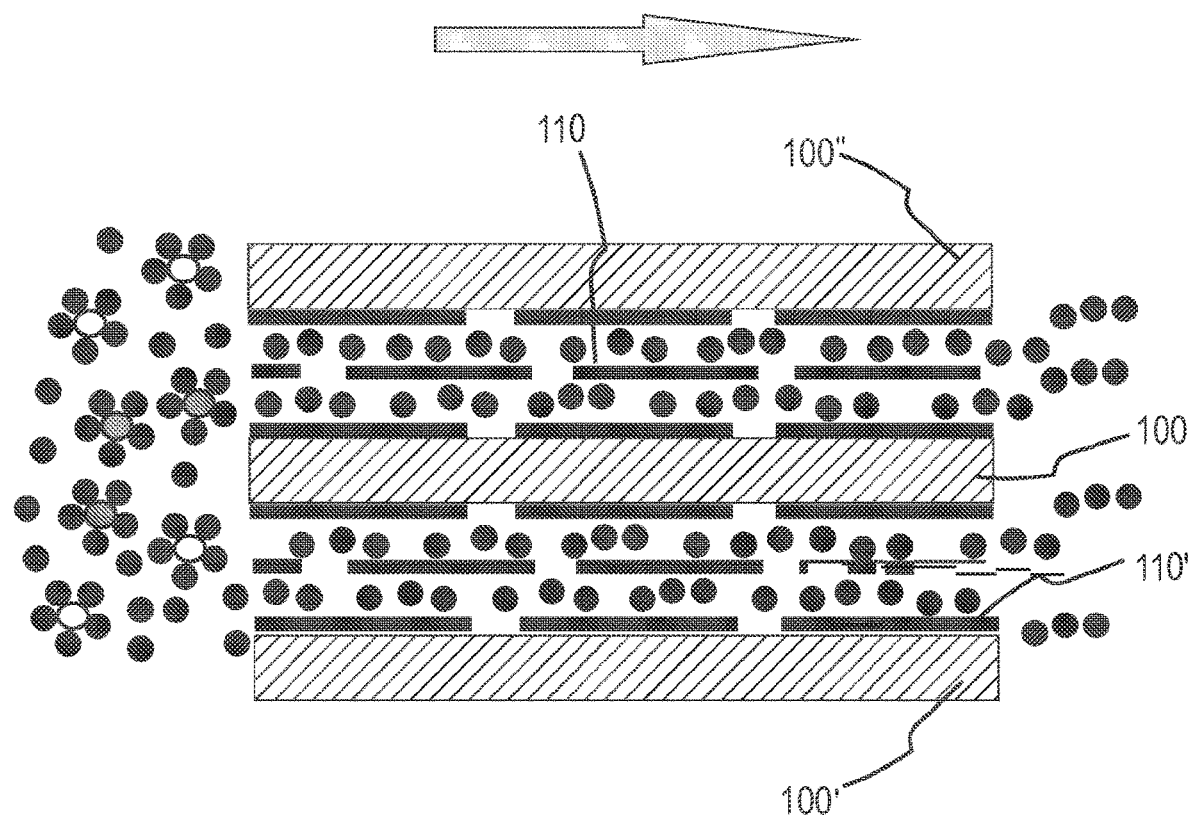
FIG. 1 is a highly diagrammatic representation of physically confined graphene oxide membranes showing the direction of NaCl permeation along the graphene planes. It will be noted that Na and Cl ions are retained on the feed/retentate side of the membranes.
Figure 1:
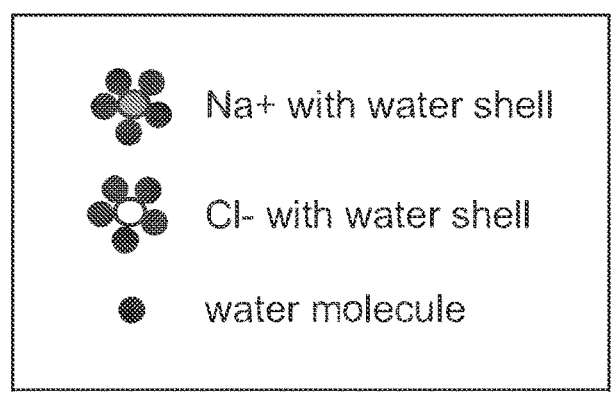

After considering this description it will be apparent to one skilled in the art how the invention is implemented in various alternative embodiments and alternative applications. However, although various embodiments of the present invention will be described herein, it is understood that these embodiments are presented by way of example only, and not limitation. As such, this description of various alternative embodiments should not be construed to limit the scope or breadth of the present invention. Furthermore, statements of advantages or other aspects apply to specific exemplary embodiments, and not necessarily to all embodiments covered by the claims.

Throughout the description and the claims of this specification the word "comprise" and variations of the word, such as "comprising" and "comprises" is not intended to exclude other additives, components, integers or steps.

Reference throughout this specification to "one embodiment" or "an embodiment" or "some embodiments" means that a particular feature, structure or characteristic described in connection with the embodiment are included in at least one embodiment of the present invention. Thus, appearances of the phrases "in one embodiment" or "in an embodiment" or "in some embodiments" in various places throughout this specification are not necessarily all referring to the same embodiment, but may.

The present specification discloses variation advantages in respect of various embodiments of the invention. It is not suggested or represented that any particular embodiment has all the advantages disclosed herein. Some embodiments may have a single advantage only. Other embodiments may have no advantage whatsoever, and instead represent a useful alternative to the prior art.

The present invention is predicated at least in part on Applicant's finding that water which is preferentially enriched in "heavy" water molecules (i.e. water molecules having oxygen atoms of isotopes with 17, 18 or more neutrons) or "light" water molecules (i.e. water molecules having oxygen atoms of isotopes with 16 or less neutrons) is useful in the hydration of a mammal both orally/parenterally, and also topically. Accordingly, in a first aspect the present invention provides a beverage, or an industrial process water, or an industrial solvent comprising water molecules, the water molecules having oxygen or hydrogen atoms of different isotopes, the beverage being enriched in at least one of the oxygen or hydrogen isotopes, the enrichment being in reference to (i) the amount of that oxygen or hydrogen isotope in the water used to produce the beverage, or the industrial process water, or the industrial solvent, or (ii) the amount of that oxygen or hydrogen isotope in ground water, or (iii) Vienna Standard Mean Ocean Water.

As used herein, the term "beverage" is intended to include any drink suitable for animal consumption, including substantially pure water products.

As used herein, the term "industrial process water" is intended to include any water, or composition containing predominantly water, that is used at an industrial scale.

As used herein, the term "industrial solvent" is intended to include any water, or composition containing predominantly water, that is used at an industrial scale to dissolve a solute, or to maintain a solute in solution, or to dilute a solvent in solution.

The term "industrial" as used herein is intended to exclude applications at a laboratory scale or a small pilot scale. Industrial processes are those used to produce goods in commercial quantities, and to supply a population of at least about 1,000 or 10,000 or 100,000 or 1,000,000 or 10,000,000, or 50,000,000 or at least 100,000,000 persons. Alternatively, an industrial process may be considered to a process capable of producing a product to an amount of 10 or 100 or 1,000 or 10,000 or 100,000 kg over a period of a period of alternatively one day or one week or one month or one year.

In a second aspect the present invention provides a topical dermatological composition comprising water molecules, the water molecules having oxygen or hydrogen atoms of different isotopes, the beverage being enriched in at least one of the oxygen or hydrogen isotopes, the enrichment being in reference to (i) the amount of that oxygen or hydrogen isotope in the water used to produce the beverage or (ii) the amount of that oxygen or hydrogen isotope in ground water, or (iii) Vienna Standard Mean Ocean Water. As used herein, the term "topical dermatological composition" is intended to include any composition suitable for application to the skin of an animal, including substantially pure water products.

The level of enrichment of any given oxygen or hydrogen isotope in the water of the beverage may be defined by reference to a comparison water. The comparison water may be the water used to produce the beverage which may be municipal water supply, or a natural water supply such as river water or spring water or rain water.

Alternatively, the comparison water is an isotopically neutral water such as ground water, or an isotopically standard water such as Vienna Standard Mean Ocean Water (VSMOW).

The enrichment may be calculated based on the total number of oxygen or hydrogen atoms for an isotope in the beverage compared with the total number of oxygen or hydrogen atoms in the comparison water. As a basic example to illustrate the principle: where the comparison water has 99 atoms of the isotope 16O and 1 atom of the isotope 18O (for a total of 100 atoms), and the beverage water has 98 atoms of 16O and 2 atoms 18O (for a total of 100 atoms) then the enrichment for 18O can be expressed as 1 molecule per 100 total molecules.

The level of enrichment may be at least about 1 molecule per 1000000 total molecules, 1 molecule per 100000 total molecules, 1 molecule per 10000 total molecules, 1 molecule per 1000 total molecules, 1 molecule per 900 total molecules, 1 molecule per 800 total molecules, 1 molecule per 700 total molecules, 1 molecule per 600 total molecules, 1 molecule per 500 total molecules, 1 molecule per 400 total molecules, 1 molecule per 300 total molecules, 1 molecule per 200 total molecules, 1 molecule per 100 total molecules, 1 molecule per 90 total molecules, 1 molecule per 80 total molecules, 1 molecule per 70 total molecules, 1 molecule per 60 total molecules, 1 molecule per 50 total molecules, 1 molecule per 40 total molecules, 1 molecule per 30 total molecules, 1 molecule per 20 total molecules or 1 molecule per 10 total molecules.

The enrichment of heavy water molecules or light water molecules may be set at a predetermined level, or toward a predetermined level, or in accordance with a desired result. For example, where a beverage is to be used to facilitate sweating to decrease body temperature during physical exertion, the beverage water may be enriched for light water molecules. Applicant proposes that light water molecules secreted in sweat evaporate from the skin surface more easily, and are therefore have a higher capability of removing the latent heat of vaporisation from the skin as compared with heavy water molecules. Removal of the latent heat of vaporisation acts to cool the skin, and assist in maintaining or decreasing body temperature. By contrast, a beverage enriched in heavy water molecules may be used where water loss from the skin surface is to be avoided, for example to improve hydration of the skin for functional or cosmetic reasons, or to otherwise avoid water loss from the body.

In the case of a topical dermatological composition, the water molecules may be enriched in heavy water so as to avoid evaporation of water from the skin. Thus, the composition is deposited on the surface of the skin (by a spray, of by manual application) thereby forming a film of water molecules over the skin. The film is enriched in heavy water molecules and so has a lower propensity for evaporation. The skin therefore remains hydrated to a greater level and/or for a greater time period as compared with a composition not enriched in heavy water molecules.

In some situations, a dermatological composition enriched in light water molecules may be required. As an example, the composition may be a spray which is intended to assist in cooling the body in hot weather. In that case, the light water molecules are more likely to evaporate than heavy water molecules, and therefore more capable of removing the latent heat of vaporization from the skin.

The source of water from which the beverage or dermatological composition is produced may be naturally enriched in heavy water or light water. For example, water molecules present ground water, surface water, sea water, lakes, rivers, precipitation, snow, ice derived from precipitation, and glacial ice will all have differing ratio of heavy water molecules to light water molecules. The ratio also varies according to the location of the water source, and in particular the atmospheric temperature of the location. In the context of the present invention the water molecules used to produce the dermatological compositions or the beverages may be obtained from a natural source which is already enriched with heavy or light water molecules. In other embodiments, the water used to produce the dermatological compositions or the beverages is modified by any means deemed useful by the skilled artisan to result in an enrichment of at least one oxygen or hydrogen isotope.

The level of enrichment of heavy water to light water molecules may be expressed by reference to means known in the meteorological, geochemical, paleoclimatological and paleocenanographical arts by reference to a the delta-18-O value. This value is a measure of the ratio of stable isotopes 18O:16O, and is commonly used as a measure of the temperature of precipitation, as a measure of groundwater/mineral interactions, and as an indicator of processes that show isotopic fractionation, such as methanogenesis. In paleosciences, 18O:16O data from corals, foraminifera and ice cores are used as a proxy for temperature. The definition is, in "per mil" (‰, parts per thousand), and calculated as follows:

$$\delta^{18}O = \left( \frac{\left(\frac{18_O}{16_O}\right)_{sample}}{\left(\frac{18_O}{16_O}\right)_{standard}} - 1 \right) * 1000\%$$

where the standard has a known isotopic composition, such as Vienna Standard Mean Ocean Water (VSMOW). A consideration of delta-18-O was hitherto unknown in the medical, cosmetic, or beverage production arts, however Applicant proposes that the value has use in describing the present beverages, compositions and methods.

Methods for determining delta-18-O are well known to persons skilled in the meteorological, geochemical, paleoclimatological and paleocenanographical arts, and the Applicant has found such methods to be useful also in the dermatological, cosmetic, beverage production or industrial process arts. Commercially available analysis units such as the model L2140-I (Picarro Inc, CA) provide high precision measurements of delta-18-O in water for applications such as paleoclimatology and oceanography. Applicant proposes that such instruments are useful also in the beverage, medical and cosmetic arts.

Given the benefit of the present specification, the skilled person is enabled to select a minimum level of heavy or light water molecule enrichment for a particular application. For some applications, the level of enrichment may be within the range of naturally occurring water while for others it may be necessary to deliberately enrich to greater levels than that found in nature.

In some embodiments, the water source may be substantially unenriched in heavy or light water molecules, or insufficiently enriched in heavy or light water molecules in consideration of the proposed use as a beverage or dermatological composition. In such circumstances, the water source may be fractionated by human intervention so as to provide a water enriched (or better enriched) in either heavy or light water molecules. Indeed, for reasons of convenience, or economy, or reproducibility the present compositions and beverages preferably contain water which has been artificially enriched in heavy or light water molecules.

In some embodiments of the invention, the source water is treated by an evaporative method. In such methods it is typical that the water is heated (optionally under vacuum) so as to cause evaporation of water molecules from the surface, and then condensing the evaporated water back to liquid water which is then collected for use in the beverage or the dermatological composition. Light water molecules preferentially evaporate, and so the condensate will be enriched in light water molecules. The unevaporated water remaining will be enriched in heavy water due to the exit of light water molecules.

In some embodiments, the water source is a plant tissue. Applicant proposes that significant advantage is provided by the use of plant tissue. One advantage is the heavy or light water that is collected comprises plant-derived ions and compounds. Fruit, vegetables and other plant materials contain phytonutrients, antioxidants, nutraceutical substances, minerals and vitamins and the like. A number of studies have demonstrated protection against chronic diseases such as heart disease, stroke, cancer and hypertension.

There are numerous types of phytonutrient types found in plant material, including alkaloids, betalains, carotenoids, chlorophyll and chlorophyllin, flavanoids, flavonoligans, Isothiocyanates, monoterpenes, organosulfides, phenolic compounds, sapanins and sterols.

Plant materials also contain water soluble vitamins such as vitamins C, B1, B2, niacin, B6, folate, B12, biotin and pantothenic acid. Water-soluble vitamins are not stored and are readily eliminated in the urine. Humans therefore require a continuous supply in the diet. Water soluble vitamins are available in many plant materials but are easily destroyed as a result of heating, exposure to air, alkaline or acidic conditions and light.

Eight of the water-soluble vitamins are known as the B-complex group: thiamin (vitamin B1), riboflavin (vitamin B2), niacin, vitamin B6, folate, vitamin Bi2, biotin and pantothenic acid. These vitamins are widely distributed in plant material. Their actions are exerted in many parts of the body, functioning as coenzymes involved in the extraction of energy from food. They also are important for appetite, vision, skin, nervous system and red blood cell formation.

Vitamin C assists in maintaining cell integrity, aids in wound healing, bone and tooth formation, strengthens the blood vessel walls, is vital for the function of the immune system, and improves absorption and utilization of iron. This vitamin also helps prevent nutritional ailments such as scurvy. Vitamin C also serves as an antioxidant, working with vitamin E as a free-radical scavenger. Studies suggest that vitamin C may reduce the risk of certain cancers, heart disease and cataracts. Vitamin C is not manufactured by the body, but must be constantly consumed. While the body has a constant need for vitamin C, it has a limited storage capacity. Accordingly, a beverage produced by a water that is enriched in heavy or light water molecules may provide further advantage to the consumer even if only trace amounts of any of the aforementioned compounds co-fractionate with a heavy or light water enriched fraction.

In the context of a topical dermatological composition, plant derived ions and compounds can provide functional or aesthetic advantage to the skin. Compounds such as vitamins are known to be useful in improving the function of appearance of skin. For example, vitamin C (from citrus fruits) and vitamin A (from carrot) have established roles in positively altering the skin to reduce wrinkles, irregular pigmentation and the like. Vitamin E (from broccoli, spinach, papaya, or avocado) is a potential free radical scavenger which protections skin from damaging oxidation. Vitamin K (from kale, onion, or asparagus) is effective in spider veins, scars, and dark circles under the eyes). Biologically active molecules in Aloe plant species are known to be beneficial for psoriasis.

Another advantage of using plant material as a source of water relates to the finding that plant-derived water is already enriched in heavy water molecules as compared with the water with which the plant has been grown. In the process of transpiration, water moves from the plant roots and exits via stomata on leaves and other structures. Light water molecules are more likely to be lost to the environment during transpiration (via the stomata) and so water remaining in the plant becomes enriched in heavy water molecules. Thus, plant-derived water (being already enriched in heavy water) useful as a beverage base, and also as a dermatological composition base. As a beverage base, the plant-derived water may be used to provide water to a person that wishes to reduce sweating and retain more water in the body. As a dermatological composition base, the heavy water is useful to provide a film over the skin which is less susceptible to evaporation.

Applicant has discovered that in extracting water from plant material that some or all of the beneficial heavy water fraction is lost in the extraction process. Accordingly, the extracted water is not useful, or is less useful, in the production of beverages or topical dermatological compositions. Thus, where an evaporative method is used to extract plant-derived water from a juice, for example, the extracted water does not comprise the number of heavy water molecules that would be expected given the number of heavy water molecules in the juice. Instead, much of the heavy water molecules appear to be lost.

Plant-derived water is often obtained as a by-product in prior art juice concentration methods. However, the by-product water has been found to be lower than expected in heavy water molecules It has been found that in order increase the yield of heavy water molecules, the evaporation process must be continued to a greater extent than would otherwise be undertaken. In prior art juice concentration methods, the juice is only partially concentrated with a significant amount of water remaining in the concentrate. For example, in commercial orange juice concentration operations the starting juice material has a water content of around 90% which is reduced by evaporation down to around 30%. Accordingly, a significant volume of water remains in the concentrate after the evaporation process. Even where the juice of sugar cane is highly concentrated to molasses, the water content of the product can be as low as 15%. However, Applicant proposes that the water remaining in the concentrate after the evaporation process is a source of heavy water molecules useful for the production of beverages and dermatological compositions.

Accordingly, it is proposed that concentration proceed to a greater extent to that usually undertaken in the preparation of juice concentrates such that the water content of the concentrate is less than about 30, 25, 20, 15, 10, 9, 8, 7, 6, 5, 4, 3, 2 or 1%. In this way, all our substantially all heavy water molecules are evaporated and then collected by way of condensate. Thus, little or no heavy water molecules are lost. We evaporation to the point of leaving substantially solid material is required, specialized equipment may be used in order to extract the last remnants of water which will be particularly rich in heavy water molecules.

Where evaporation down to a solid is required, this may be achieved by any means deemed suitable by the skilled person so long as any water removed can be recovered. For example, further heating in a vessel so as to drive off any remaining water may be implemented, with the final amounts of water being collected by a cooled condenser apparatus.

Alternatively, a commercial spray drying process may be used, optionally of the type known to those skilled in the art of food processing or pharmaceutical manufacture. In such embodiments, the water removed during the spray drying process may be condensed so as to provide a water enriched in heavy isotopic forms of water.

Where water which is very highly enriched in heavy water molecules is required, the condensate may be divided into condensate fractions, each fraction taken at subsequent stages of the evaporation process. Thus, the first fractions will comprise lower levels of heavy water molecules and the later fractions will comprise higher levels of heavy water molecules. For example, in an evaporation process the juice may be concentrated down to a water content of 20%, with the condensate being discarded or used for other purposes. The condensate obtained by way of further concentration from 20% to 5% is retained and used for a beverage or a dermatological composition due to the particularly high level of heavy water molecules.

Evaporative concentrators are known to persons skilled in the art of beverage concentrators, including multi-effect evaporator and concentrators. Suppliers of such equipment include Alfa Laval AB (Sweden) and Andritz AG (Austria).

As an alternative, or in addition to an evaporation method, source water may be fractionated be a freezing method. Without wishing to be limited by theory in any way, it is proposed that the lower activation energy and molecular weight of light water allows for light water to form ice more readily. Accordingly, were the source water is not complete frozen the unfrozen fraction will be enriched in heavy water and the frozen fraction enriched in light water. Either frozen or unfrozen fraction may be removed from the mixture as used as required.

In some embodiments, the water source or a precursor of the water source, or an intermediate product is concentrated or fractionated by a method selected from the group consisting of filtration, nanofiltration, reverse osmosis, forward osmosis, membrane distillation, or a methodology operating on the same or similar principle as any of the aforementioned methods.

Formulation of Enriched Water into a Beverage

While the water enriched with either heavy or light water molecules may be used without further modification, additives may be added in some embodiments. For example where the beverage is a sports drink, electrolytes, buffers, food acids, food bases, colouring, flavouring, and sweetener may be added to the enriched water.

Where the beverage is an energy drink, compounds such as caffeine or guarana extract may be added.

Where the beverage is a soft drink, sugar, colourings and flavourings may be added and the mixture then carbonated.

Where the beverage is for nutritional, functional, therapeutic, nutraceutical, paramedical, quasi medical or medical indications the beverage may comprise an additive such as a carbohydrate, an amino acid, a peptide, a protein, a protein hydrosylate, a vitamin, a mineral, a fat, an oil, a plant extract, a probiotic, a prebiotic or an animal extract.

In some embodiments, the beverage may be used in the administration of a pharmaceutical substance, with the pharmaceutical substance being dissolved or suspended in the beverage. It is proposed that the administration of some pharmaceutically active substances is benefitted by solubilisation or suspension with a beverage enriched in heavy water molecules, given the lower propensity for such molecule to be lost through sweating or by evaporation from the surface of the lungs or the mouth. The heavy water molecules may form a hydration shell around an active compound, thereby preventing loss of the compound.

Where the beverage is a drink mixer, the beverage may only be carbonated.

Packaging of Beverage

The beverage may be presented in the form of a drink vessel, which may have a closure (such as a lid) capable of sealing the vessel. The vessel may have a volume of less than about 1000 ml, 900 ml, 800 ml, 700 ml, 700 ml, 600 ml, 500 ml, 400 ml, or 300 ml. The vessel may be labelled with a graphic, a trademark, text (including compositional analysis, and instructions for use).

Formulation of Enriched Water into Topical Dermatological Composition

The enriched water may be used without additives (for example, as a simple spray to hydrate the skin) of may be formulated into a composition having an additive such as a dermatologically acceptable excipient.

As used herein, the term "dermatologically acceptable excipient" includes without limitation any adjuvant, carrier, glidant, diluent, preservative, dye/colorant, surfactant, wetting agent, dispersing agent, suspending agent, stabilizer, isotonic agent, solvent, or emulsifier, including those approved by the United States Food and Drug Administration as being acceptable for dermatological or therapeutic use on humans, or which are known, or are suitable for use in dermatological compositions.

The composition is preferably formulated so as to minimise skin irritation will still ensuring an appropriate hydration of the skin, and/or the transport of active compounds into the skin.

As required, and with the benefit of the present specification the skilled person is enabled to decide whether or not any buffer or salt is required to provide a required pH or ionic strength for the composition. Acceptable salts include those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like.

The pH of the dermatological composition may be adjusted, optionally to between about 6.0 and 8.0 using an acid, such as a food acid. The acid for adjusting the pH value can be any conventionally used organic or inorganic acid or mixtures thereof, and is preferably citric acid.

Furthermore, a buffering agent may be included so as to maintain pH at a predetermined level. Useful agents for adjusting pH, buffering or otherwise altering the ionic conditions of a composition include (by name, CAS No., ELINCS No); 1,6-hexanediamine 124-09-4, 204-679-6; 2-aminobutanol, 96-20-8, 202-488-2; acetic acid, 64-19-7, 200-580-7; acetyl mandelic acid, 51019-43-3/7322-88-5; adipic acid, 124-04-9, 204-673-3; alstonia scholaris bark extract, 91745-20-9, 294-689-7; aluminum glycinate, 13682-92-3/41354-48-7; aluminum lactate, 18917-91-4, 242-670-9; aluminum triformate, 7360-53-4, 230-898-1; aminoethyl propanediol, 115-70-8, 204-101-2; aminomethyl propanediol, 115-69-5, 204-100-7; aminomethyl propanol, 124-68-5, 204-709-8; aminopropanediol, 616-30-8, 210–475-8; ammonia, 7664-41-7; 231-635-3; ammonium acetate 631-61-8, 211-162-9; ammonium bicarbonate, 1066-33-7, 213-911-5; ammonium carbamate, 1111-78-0, 214-185-2; ammonium carbonate, 10361-29-2, 233-786-0; ammonium chloride, 12125-02-9, 235-186-4; ammonium glycolate 35249-89-9; ammonium hydroxide, 1336-21-6, 215-647-6; ammonium lactate, 515-98-0, 208-214-8; ammonium molybdate 12054-85-2; ammonium nitrate 6484-52-2, 229-347-8; ammonium phosphate, 7722-76-1, 231-764-5; ammonium thiocyanate, 1762-95-4, 217-175-6; ammonium vanadate, 7803-55-6, 232-261-3; ascorbic acid, 50-81-7/

62624-30-0, 200-066-2/263-644-3; azelaic acid, 123-99-9; 204-669; babassu acid; bakuhan; benzilic acid, 76-93-7, 200-993-2; bis-hydroxyethyl tromethamine, 6976-37-0, 230-237-7; bismuth citrate, 813-93-4, 212-390-1; boric acid, 10043-35-3/11113-50-1, 233-139-2/234-343-4; butyl diethanolamine, 102-79-4, 203-055-0; calcium carbonate, 471-34-1, 207-439-9; calcium citrate 813-94-5, 212-391-7; calcium dihydrogen phosphate, 7758-23-8, 231-837-1; calcium glycinate, 35947-07-0, 252-809-5; calcium hydroxide, 1305-62-0; 215-137-3; calcium lactate, 814-80-2, 212-406-7; calcium oxide, 1305-78-8, 215-138-9; calcium phosphate, 7758-23-8/10103-46-5, 231-837-1/233-283-6; citric acid 77-92-9/5949-29-1, 201-069-1; clay minerals; copper glycinate, 32817-15-5, 251-238-9; diammonium citrate, 3012-65-5, 221-146-3; diammonium phosphate, 7783-28-0, 231-987-8; dibutyl ethanolamine, 102-81-8, 203-057-1, diethyl ethanolamine, 100-37-8, 202-845-2; dimethyl isopropanolamine, 108-16-7, 203-556-4; dimethyl mea, 108-01-0, 203-542-8; dioleoyl edetolmonium methosulfate, 111030-96-7; dioleyl phosphate, 14450-07-8, 238-431-3; dipotassium phosphate, 7758-11-4, 231-834-5; disodium fumarate, 17013-01-3, 241-087-7; disodium phosphate, 7558-79-4/7782-85-6, 231-448-7; disodium pyrophosphate, 7758-16-9, 231-835-0; disodium tartrate, 868-18-8, 212-773-3; ethanolamine, 141-43-5, 205-483-3; ethanolamine HCL, 2002-24-6, 217-900-6; ethyl ethanolamine, 110-73-6, 203-797-5; fumaric acid, 110-17-8, 203-743-0; galacturonic acid, 685-73-4, 211-682-6; glucoheptonic acid, 23351-51-1, 245-601-0; gluconic acid, 526-95-4, 208-401-4; glucuronic acid, 576-37-4; 209-401-7; glutaric acid, 110–94-1, 203-817-2; glycine, 56-40-6, 200-272-2; glycolic acid, 79-14-1201-180-5; glyoxylic acid, 298-12-4, 206-058-5; guanidine carbonate, 593-85-1, 209-813-7; guanidine HCl, 50-01-1, 200-002-3; hydrobromic acid, 10035-10-6, 233-113-0; hydrochloric acid, 7647-01-0, 231-595-7; hydroxyectoin, 165542-15-4, 442-870-8; hydroxyethylpiperazine ethane sulfonic acid, 7365-45-9, 230-907-9; imidazole, 288-32-4, 206-019-2; isobutyric acid, 79-31-2, 201-195-7; isopropanolamine, 78-96-6, 201-162-7; isopropylamine 75-31-0200-860-9; lactic acid, 50-21-5, 200-018-0; lactobionic acid, 96-82-2, 202-538-3; lauryl p-cresol ketoxime, 50652-76-1; lithium carbonate, 554-13-2, 209-062-5; lithium hydroxide, 1310-65-2, 215-183-4; magnesium acetate, 142-72-3, 205-554-9; magnesium carbonate hydroxide, 12125-28-9, 235-192-7; magnesium glycinate, 14783-68-7, 238-852-2; magnesium hydroxide, 1309-42-8, 215-170-3; magnesium lactate, 18917-93-6, 242-671-4; magnesium oxide, 1309-48-4, 215-171-9; maleic acid, 110-16-7, 203-742-5; malic acid, 97-67-6, 202-601-5; malonic acid, 141-82-2, 205-503-0; maltobionic acid 534-42-9; mea-borate, 10377-81-8, 233-829-3; metaphosphoric acid, 37267-86-0, 253-433-4; methoxy peg-100/polyepsilon caprolactone ethylhexanoate; methoxypeg-100/polyepsilon caprolactone palmitate; methoxy peg-114/polyepsilon caprolactone; methylethanolamine, 109-83-1, 203-710-0; monosodium citrate, 18996-35-5, 242-734-6; mudstone powder; paecilomyces japonica/grape/cucumber juice extract ferment filtrate; pentapotassium triphosphate, 13845-36-8, 237-574-9; pentasodium triphosphate, 7758-29-4, 231-838-7; phenolsulfonphthalein, 143-74-8, 205-609-7; phenyl mercuric borate, 102-98-7, 203-068-1; phosphonobutanetricarboxylic acid, 37971-36-1, 253-733-5; phosphoric acid, 7664-38-2, 231-633-2; phosphorus pentoxide, 1314-56-3, 215-236-1; potassium bicarbonate, 298-14-6, 206-059-0; potassium biphthalate, 877-24-7, 212-889-4; potassium bitartrate, 868-14-4, 212-769-1; potassium borate, 1332-77-0, 215-575-5; potassium carbonate, 584-08-7, 209-529-3; potassium citrate, 866-84-2, 212-755-5; potassium hydroxide, 1310-58-3, 215-181-3; potassium lactate, 996-31-6/85895-78-9, 213-631-3/288-752-8; potassium magnesium aspartate, 67528-13-6; potassium oxide, 12136-45-7, 235-227-6; potassium phosphate, 7778-77-0/16068-46-5, 231-913-4/240-213-8; potassium sodium tartrate, 304-59-6, 206-156-8; potassium tartrate, 921-53-9, 213-067-8; propane tricarboxylic acid, 99-14-9/51750-56-2, 202-733-3; quinic acid, 77-95-2/562-73-2/36413-60-2, 201-072-8/209-233-4; ribonic acid, 17812-24-7; sebacic acid, 111-20-6, 203-845-5; sesquiethoxytriethanolamine; sh-decapeptide-7; sodium acetate, 127-09-3, 204-823-8; sodium aluminate, 1302-42-7, 215-100-1; sodium aluminum lactate, 68953-69-5, 273-223-6; sodium arachidate; sodium aspartate, 17090-93-6/3792-50-5, 241-155-6/223-264-0; sodium bicarbonate, 144-55-8, 205-633-8; sodium bisulfate, 7681-38-1, 231-665-7; sodium borate, 1330-43-4/1303-96-4 215-540-4; sodium butoxyethoxy acetate, 67990-17-4, 268-040-3; sodium calcium boron phosphate; sodium calcium copper phosphate; sodium calcium zinc phosphate; sodium carbonate, 497-19-8, 207-838-8; sodium citrate, 68-04-2/6132-04-3, 200-675-3; sodium esylate, 5324-47-0, 226-194-9; sodium formate, 141-53-7, 205-488-0; sodium fumarate 5873-57-4/7704-73-6, 227-535-4/231-725-2; sodium glycolate, 2836-32-0, 220-624-9; sodium humate, 68131-04-4; sodium hydroxide, 1310-73-2, 215-185-5; sodium lactate, 72-17-3/867-56-1, 200-772-0/212-762-3; sodium metaphosphate, 10361-03-2/50813-16-6, 233-782-9/256-779-4; sodium metasilicate, 6834-92-0, 229-912-9; sodium oxide, 1313-59-3, 215-208-9; sodium phosphate, 7558-80-7/7632-05-5, 231-449-2/231-558-5; sodium sesquicarbonate, 533-96-0, 208-580-9; sodium silicate, 1344-09-8, 215-687-4; sodium succinate, 2922-54-5, 220-871-2; sodium trimetaphosphate, 7785-84-4, 232-088-3; strontium hydroxide 18480-07-4/1311-10-0, 242-367-1; succinic acid, 110-15-6; 203-740-4 sulfuric acid, 7664-93-9, 231-639-5; tartaric acid, 133-37-9/147-71-7/87-69-4, 205-105-7/205-695-6/201-766-0; taurine, 107-35-7, 203-483-8; tea-diricinoleate/ipdi copolymer, 351425-02-0; tea-hydroiodide 7601-53-8, 231-508-2; tea-sulfate, 7376-31-0, 230-934-6; tetrahydroxyethyl ethylenediamine, 140-07-8, 205-396-0; tetrapotassium pyrophosphate, 7320-34-5, 230-785-7; tetrasodium pyrophosphate, 7722-88-5, 231-767-1; triethanolamine, 102-71-6, 203-049-8; triisopropanolamine, 122-20-3, 204-528-4; trisodium phosphate; 7601-54-9, 231-509-8; trisodium sulfosuccinate, 13419-59-5, 236-524-3; *Triticum vulgare* protein, 100684-25-1, 309-696-3; *Triticum vulgare* seed extract, 84012-44-2, 281-689-7; tromethamine, 77-86-1, 201-064-4; urea, 57-13-6, 200-315-5; uric acid, 69-93-2, 200-720-7; zinc carbonate hydroxide, 150607-22-0; zinc glycinate, 14281-83-5, 238-173-1; zinc hexametaphosphate, 13566-15-9, 236-967-2; and zinc magnesium aspartate.

Where a surfactant is included, the surfactant can be any conventionally used anionic, cationic, nonionic, zwitterionic or amphetoric surfactant or mixtures thereof.

The composition may be formulated as a simple aqueous solution/suspension but may also be formulated with the assistance is a viscosity-increasing agent such as a gum, a gel, an agar, or a hydrogel.

The present compositions may be formulated as a cream (with an aqueous or non-aqueous base, or a mixed base—oil in water or water in oil), a foam, a foaming solution, a lotion, a balm, a soap, a serum, or a cleanser.

In some embodiments, the dermatological composition is used in the administration of a dermatologically active substance such as a transdermal pharmaceutical substance.

Where the composition is enriched in heavy water, the pharmaceutical substance may remain in solution for longer (given the lower rate of evaporation from the skin) and/or contacting the skin for a longer period of time.

In some embodiments, the water source or a precursor of the water source, or an intermediate product is concentrated or fractionated by a method selected from the group consisting of a nanofiltration, reverse osmosis, forward osmosis, membrane distillation, or a methodology operating on the same or similar principle as any of the aforementioned methods.

Packaging of Topical Dermatological Composition.

The composition may be presented in the form of a spray vessel configured to dispense a fine mist over the skin to provide a thin film of composition. Where the composition is viscous (such as in the form of a cream or a lotion) the vessel may be in the form of a tube, a bottle, a sachet, or a jar and have a closure capable of sealing the vessel. The vessel may be labelled with a graphic, a trademark, text (including compositional analysis, and instructions for use).

Where the composition is to be applied to the face only, and packages of relatively small volume will be useful, such as less than 100 ml, 90 ml, 80 ml, 70 ml, 60 ml, 50 ml, 40 ml, 30 ml, 20 ml and 10 ml.

The dermatological composition may be used to impregnate a wipe, with the wipe being sealed within a sachet. Alternatively, a plurality of wipes may be interleaved and packaged in a container capable of being sealed after removal of a wipe for use. Such wipes may be useful for make-up removal or as an infant wipe; in which case the composition used to impregnate the wipe may comprise a detergent, a soap, a cleanser, a mild exfoliant, a fragrance, an antibacterial, an anti-inflammatory, a skin demulcent, or the like.

The present compositions are typically implemented by the user by spraying, spreading, gently rubbing or massaging the composition onto the skin of an animal. In the context of the present invention the term "animal" is intended to include without limitation any mammal such as a human, primate, domestic animal, beast of burden, zoo animal, agriculturally or economically significant animal. As will be appreciated, given the aesthetic and functional advantages of the present compositions as disclosed herein it is the primary intention that the compositions are formulated so as to be useful in application to humans, and in particular the skin of the face or upper torso.

The composition may be used in a dermatologically effective amount, which refers to that amount which, when administered dermatologically (i.e., topically) to an animal, is sufficient to effect the desired effect, such as the desired amount of hydration or the desired amount of an active substance carried by the composition. The amount of composition which constitutes a dermatologically effective amount may vary depending on, the condition of the skin and the need for improvement, and the age of the animal to be treated, but can be determined routinely by one of ordinary skill in the art having regard to his own knowledge and to this disclosure.

In a further aspect, the present invention provides a method of performing an industrial process, the method comprising the step of contacting an industrial process water as described herein to an item of industrial equipment.

In another aspect, the present invention provides a method of forming a solution of a solute or a liquid mixture at an industrial scale, the method comprising the step of providing a solute or liquid and contacting the solute with an industrial solvent according as described herein.

Yet a further aspect of the present invention provides a method of diluting a solution at an industrial scale, the method comprising the step of providing a solution and contacting the solution with an industrial solvent as described herein.

Dairy Material as a Source of Isotopically Enriched Water.

In addition or as an alternative to the plant sources described elsewhere herein, it is contemplated that animal-derived material will be useful as a water source for beverages or dermatological compositions, or even process water. An exemplary material is a diary material as provided by the milking of an animal (such as an ungulate, and particularly ungulates of the genus *Bos*).

While a milk may be used directly as a water source, it is preferable to utilise a milk derivative. Preferably the milk derivative is a by product or a low value product such as whey or a filtration permeate. Such derivatives can be formed in considerable volumes in industrial scale methods for making cheese, yoghurt, protein concentrates, and protein powders for example.

Dairy material (including derivatives thereof, such as whey) may in some forms be already enriched in heavy water or light water, and therefore not require any treatment to modify isotopic composition. Where isotopic enrichment is required, any of the means disclosed elsewhere herein may be utilised, or indeed any other method deemed suitable by the skilled artisan.

Spent Wash as a Source of Isotopically Enriched Water.

Spent wash is an unwanted liquid waste generated in the course of alcohol production and distillation. This by-product is formed in large volumes and is typically discarded as waste at some cost to the manufacture given the need remediation treatment before discharge. Spent wash represents a significantly wastage of water in the distillation industry, and by virtue of the present invention may be recovered and treated so as to provide a ready source of process water that may be used elsewhere in the same production facility, as discussed infra.

Spent wash may in some forms be intrinsically enriched in heavy water or light water, and therefore not require any treatment to modify isotope composition. Where isotopic enrichment is required, any of the means disclosed elsewhere herein may be utilised, or indeed any other method deemed suitable by the skilled artisan.

As discussed elsewhere herein, spent wash may be treated by a separative method (such as by a molecular sieve).

Water Drawn from a Natural Body as a Source of Isotopically Enriched Water.

Water from a natural source may be used because of its intrinsic enrichment in heavy or light water molecules, or for its potential to be treated so as to be enriched in heavy or light water. For example, the ocean is a plentiful source of water and may be drawn upon as a starting material for any method or product of the present invention.

For many application, the high concentration of salts (such as sodium chloride) contraindicates use. For example, where the end use is process water for washing industrial equipment the presence of salts may leave a residue upon drying which may contaminate any material under processing. High levels of salt may render a beverage unpalatable or a dermatological composition irritating to the skin.

Salts and other undesirable solutes may be directly removed by use of a molecular sieve (as more fully described infra) configured to have a sieve size smaller than the diameters of hydrated sodium and chloride ions. Other means for removing salt including forward osmosis and reverse osmosis may be utilised.

Where forward osmosis is used, a molecular sieve may be used to regenerate the draw solution. For example, the solute in the draw solution may be chosen so as to be substantially incapable of passing through a sieve having a pore size that allows the passage of water molecules.

Applications of the Invention to Producing Industrial Process Water

Applicant proposes that water enriched in light water molecules or heavy water molecules is useful as an industrial process water. In the context of the present invention, the process water may be produced from any source material, including those explicitly disclosed herein. Furthermore, the process water may be enriched in heavy or light water molecules in accordance with any method disclosed herein, or indeed any other method. In some embodiments, the process water is not produced by any dedicated method and may instead arise due to a natural process, or in the course of an industrial process performed for a purpose other than the production of an isotopically enriched water.

The process water of the present invention may, for example, be useful in a water cooling tower of an air conditioning system. Such systems relies on the evaporation of water, with the heat of evaporation being drawn from air circulating through the cooling tower, thereby cooling the air. Water having a higher proportion of lighter water molecules will more readily transition from the liquid phase to the vapour phase, and accordingly will more readily withdraw the latent heat of vaporization from their air. This may result in more rapid or more efficient or more complete air cooling.

In another example, a process water enriched in light water molecules may be used in an industrial scale boiler for the creating of water vapour or steam. Again, because of the greater propensity for light water molecules to leave the liquid phase, vapour or steam is more readily generated. Less input energy (such as electrical energy) may be required to produce the same amount of water vapour or steam as compared with water that is not isotopically enriched.

Industrial process waters are used extensively in washing and rinsing of equipment such as storage vats, fermenters, mixers, conduits and the like. Typically, the equipment should be dry before use, with the drying process taking time and optionally energy (such as air blowers). The use of process water enriched in light water molecules will facilitate drying given the greater propensity for such water to evaporate.

In some industrial processes it may be preferred to avoid evaporation of water, in which case process water enriched in heavy molecules may be used. In one such application, water may be used for soaking a vessel in a cleaning protocol, and the use of water that is less prone to evaporation will be advantageous.

The source of the industrial process water may be any source deemed suitable by the skilled person having the benefit of the present specification. The process water may be any source explicitly described elsewhere herein, and particularly the juice of a fruit, a vegetable, sugarcane, sugar beet, a trees or any other plants. Preferably, the process water is sourced from the low sugar juice remaining as waste after a juice concentration process.

During removal of water from juice by any concentration process, the heavy water preferentially remains with the juice concentrate, unless all the water is removed from the solids. Water removed from juice has a higher ratio of light to heavy water when compared to the ratios found in the source juice before fractionation, making it a preferred water for use in boilers and cooling towers.

In some circumstances, the industrial process water is derived from a process waste stream of a juice concentration process, and the process water is returned for use into the originating juice concentration process or indeed any other process.

Applications of the Invention to Producing a Water for Introduction Into an Industrial Process.

As distinct from the generation of process water, the present invention may be further exploited to provide a water which is used as a solvent in an industrial process. Water is commonly used to dissolve solutes or to act as a diluent of solutions already formed. It in any event, it is proposed that the use of water being enriched in either heavy or light water is advantageous. For example, the heat of solution of various solutes (such as salts) may be variable depending on the proportions of heavy and light water in the solvent water. There is also a solvent isotope effect which alters the stability of proteins (and particularly the stability of protein folding) in aqueous solution. Furthermore, there is a strong water isotope effect on the formation of ice crystals. Accordingly, heavy or light water as a solvent can be used to exploit one of many solvent isotope effects in an industrial process.

In one preferred embodiment, spent wash which is intrinsically enriched in heavy or light water or is to be enriched in heavy or light water, or has been enriched in heavy or light water may be used as a diluent to dilute sugars in a fermentation process down to a desired concentration. Thus, a fermentation process used to produce alcohol may produce a spent wash by-product, with the spent-wash by product being returned to the process for use as a sugar diluent. In this way, water is retained within the system and the need to remediate spent wash for discharge is decreased.

Where a water is used as a solvent in an industrial process, it would be generally pre-treated in some manner. In the example of spent wash, significant treatment of a separative process such as a filtration process and/or an at least partially adsorptive process such as contact with granular activated carbon may be required to remove impurities down to process-acceptable concentrations. In some embodiments the spent wash is filtered directly through a molecular sieve so as to remove the vast majority of the plurality of impurities contained therein. Alternatively, a forward or reverse osmosis method may be used, and in the case of the former method a molecular sieve may be used to regenerate the draw solution.

Use of Molecular Sieves

As discussed elsewhere herein, various means are proposed for the enrichment of heavy water molecules over light water molecules and vice-versa. An alternative or additional means may be provided by filtration using graphene sieve technologies.

Molecular sieve technology may be furthermore used to pre-treat solutions which are to be enriched for heavy or light water, and also treat solutions which are already enriched in heavy or light water, or is intrinsically enriched for a heavy or light water so as to confer suitability for an intended use. Such pre- and post-treatment may be selected so as to remove a salt, an organic molecule, an inorganic molecule, a gas, a particle, or a microbe.

Molecular sieves may also find utility in the context of the present invention as means to regenerate a draw solution for any forward osmosis method used to as a treatment for heavy or light enriched water, or to pre-treat a solution that is to be enriched for heavy or light water, or is intrinsically enriched for a heavy or light water.

As is well understood by the skilled person, forward osmosis is a membrane-based separation method that relies on a concentrated draw solution having high osmotic potential to draw water across a semi-permeable membrane from a feed source. The product of forward osmosis is not purified water, but instead a diluted draw solution which must be regenerated so as to draw more water across the membrane. A second purification step is often required in a forward osmosis protocol to produce a pure water product. Advantageously, forward osmosis involves a low hydrodynamic pressure, leading to lowered fouling of membranes and greater recovery of flux after cleaning. Forward osmosis can be considered as a low energy process which can recover clean water from any of the water sources disclosed herein.

The draw solution solute may be selected so as to be substantially incapable of passing through the molecular sieve. Alternatively, the molecular sieve may be configured so as to be substantially incapable of passing the selected draw solution solute, while being permeable to water molecules. Draw solutions that can be regenerated by a size-based separative process include organic compounds such as glucose, fructose, sucrose, ethanol, sodium formate, sodium acetate, sodium propionate, magnesium acetate; inorganic salts such as sodium chloride, potassium bromide, sodium bicarbonate, potassium bicarbonate, magnesium chloride, sodium sulfate, potassium sulfate, and magnesium sulfate.

The skilled person is aware of a range of draw solutes, and accordingly is enabled to tune a molecular sieve so as to selectively pass water but retain the solute.

Molecular sieves may be used, for example, directly or indirectly to treat a water source. As an example of direct application, a graphene sieve may be used to treat whey so as to remove the various ions, proteins (such as casein), peptides, amino acids, and other organic molecules (such as sugars) which are contained (albeit at low levels) in whey. While theses sieves are very effective, trace levels of solute may enter the permeate and be detectable in the process water, beverage or dermatological composition this is, or that is derived from, the purified permeate. Such low levels will generally not adversely affect the end use, and will in some circumstances provide a means for identifying the whey source of any process water, beverage or dermatological composition.

As an example of the indirect application of a molecular sieve, such a sieve may be used to regenerate a draw solution in forward osmosis purification method of a solution which is to be enriched for heavy or light water, or has already been enriched in a heavy or light water, or is intrinsically enriched for a heavy or light water. As discussed above, molecular sieves are capable of retaining salts, and will therefore have utility in regeneration of a draw solution.

Other purification modalities may be applied to the whey, or any treated whey, to confer suitability for use. As one example, an activated carbon step may be implemented to remove solutes such as aromatics and other volatiles. Separative methods such as forward osmosis, reverse osmosis, ultrafiltration, microfiltration, nanofiltration, preparative chromatography and the like may also be used in this context.

Molecular sieve technology may be applied to any water source derived from a plant material (such as any of those disclosed elsewhere herein) for the purpose of producing a beverage. In this context, it is preferable that the water source has been enriched in a heavy water or a light water, or is to be enriched in a heavy water or a light water, or is intrinsically enriched in a heavy water or a light water. A molecular sieve may be used to derive a substantially purified water from plant water, with the water so derived being potentially being further treated (if necessary) to be potable. Accordingly, sterilization techniques (including separative, chemical, and physical means) may be used, and optionally with the addition of a chemical preservative if necessary to extend shelf life. Treatment with activated carbon may be required to remove molecules which may adversely affect the taste and/or aroma of the beverage product.

Molecular sieve technology may be applied to spent wash, or a treated (such as remediate) spent wash, or a spent wash that has been enriched in a heavy water or a light water, or a spent wash is to be enriched in a heavy water or a light water, of a spent wash that is intrinsically enriched in a heavy water or a light water. A molecular sieve may be used to derive a substantially purified water from the spent wash, with the water potentially being used elsewhere in the alcohol production process from which it was created, or indeed any other process. The resultant water may alternatively be used in a beverage or a dermatological composition, although adjunctive methods such as treatment with activated carbon may be required to remove molecules which may adversely affect the taste and/or aroma of the resultant product.

As used herein, the term "molecular sieve" is intended to include any material that is able to discriminate solutes from solvents (and particularly discriminate ionic solutes from water molecules), and/or solutes from solutes, and/or solvents from solvents on the basis of a differential in size of the respective species. In some forms, a molecular sieve may separate at least to some extent also on the basis of charge or hydrophobicity or some adsorptive property. These sieves may comprise pores of substantially uniform size, or have a pore size within a defined range. The pore diameters are typically similar in size to smaller species, and thus larger species cannot enter into or be adsorbed onto the material, while smaller species may. As a mixture of species migrate through the sieve (or matrix), the species of highest molecular weight or diameter (which are unable to pass into the molecular pores) exit the bed first, followed by successively smaller species.

The pore diameter of a molecular sieve is typically measured in ångströms (Å) or nanometres (nm). Some sieves may be considered microporous having pore diameters of less than 2 nm (20 Å), or macroporous materials having pore diameters of greater than 50 nm (500 Å), or mesoporous having pore diameters between 2 and 50 nm (20-500 Å).

The molecular sieve may be naturally occurring (such as a mineral) or be manufactured (such as a graphene).

Molecular sieves useful in at least some embodiments of the invention may include graphene (hexagonal lattice) or graphene oxide or boron-nitride. Each may exist as monolayers or multilayers and containing physical pores or channels of different sizes, and may even have an electrical gradient to assist barrier movement.

For these sieves to be permeable and useful for desalination, small and very uniform pores in the membrane are required. If the pore size is larger than about 1 nanometre, the salts will penetrate and not be separated from the water molecules. Size exclusion is the aim of the engineered sieve pore sizes required to separate salts from the different isotopic varieties of water.

Graphene oxide can be multilayered with appropriate interlayer spacing for the particular application, for example less than about 10 Angstroms. The interlayer spacing may be controlled and produce pores or channels that are smaller than the overall size of common salts surrounded by water molecules. The salt species is surrounded by an outer "shell" of water molecules, with the size of the shell being a determinant in whether or not the salt species is excluded from the molecular sieve.

Interlayer spacing size may be adjusted to produce channels that allow a specific isotopic water species to pass through without allowing significant amounts of salts or minerals to follow the water. For example, graphene oxide sheets with desired sizes and narrow size distribution may be synthesized via a modified Hummers method by the use of sieved graphite flakes as the starting material. This method is a preferred alternative to post-synthesis fractionation methods in terms of efficiency and scalability and is therefore advantageous in large-scale applications.

Pore sizes and therefore (permeation cut-offs) can be finely tuned, down to a size of around 9 Å. This size will allow passage of hydrated ions of common salts. The cut-off may be determined by interlayer spacing (d) of about 13.5 Å, that spacing being typically noted for graphene laminates upon swelling in an aqueous environment.

Smaller interlayer spacing (and therefore lower cut-offs) can be achieved by controlling the interlayer spacing by physical confinement of the laminate. Physical confinement may be controlled so as to achieve accurate and tuneable ion sieving. Membranes with d from about 9.8 Å to 6.4 Å can be prepared, providing the sieve size smaller than the hydrated diameter of a typical ion. Ion permeation is found to be thermally activated with energy barriers of about 10-100 kJ/mol depending on d. Permeation rates are found to decrease exponentially with decreasing sieve size but water transport is weakly affected (by a factor of <2). The latter is due to a low barrier for water molecule entry and large slip lengths inside graphene capillaries. Such graphene-based membranes exhibited limited swelling, and provide 97% rejection for NaCl.

In this way, a tunable sieve having spacing down to 6.4 Å can be produced thereby providing a sieve size smaller than the diameters of hydrated ions. Such as sieve may almost completely reject NaCl whilst allowing passage of water molecules.

In a preferred form of the invention thick ~100 μm) graphene oxide laminates are prepared by vacuum filtration of aqueous graphene solutions as reported by Kumar and colleagues (J. Comput. Chem. 13, 1011-1021 (1992)). The laminates are cut into strips and stored at different relative humidities (RH), achieved using saturated salt solutions. The interlayer spacing is measured by X-ray diffraction and may vary from about 6.4 to 9.8 Å with RH changing from zero to 100%. Graphene oxide laminates soaked in water may show d about 13.7±0.3 Å. Changes in d may be attributed to successive incorporation of water molecules into various sites between the graphene oxide sheets.

Graphene oxide strips with desirable d are encapsulated and stacked together using Stycast™ epoxy to increase the available cross-section for filtration. The stacked laminates, now embedded in the epoxy are referred to as physically confined graphene oxide (PCGO) membranes because the epoxy mechanically restricts the laminate's swelling upon exposure to RH or liquid water. The stacks are glued into a slot made metal or plastic plate for example.

Two sides of these stacked PCGO membranes are then trimmed to ensure that all the nanochannels are open.

Reference is made to FIG. 1 showing stacked laminates (several graphene oxide membranes) marked 110, 110' physically confined by epoxy layers (100, 100', 100").

It will be appreciated that alternative means of physical confinement are available to the skilled person, with all such means included in the ambit of the present invention.

The pores in the molecular sieve may be of a size that is less than about 1 nanometre which is about the size of the water molecule containing the different hydrogen or oxygen isotope. For example, $H_2O16$ molecular diameter is 0.29 nm. This diameter would exclude $H_2O17$ and $H_2O18$. Pore sizes for all other isotopic varieties of water can be tailored to selectively filter them out from either a draw solution or any water or liquid source. The diameter of these water molecules is determined mainly by the length of the hydrogen bond.

In the case of a draw regenerating role, the draw solution can be selected on the basis that the constituents, other than water, will not pass through the molecular sieve.

Selecting a specific isotopic variety of water may require two or more molecular sieves arranged in series, starting with the larger pore size appropriate for the largest isotopic water variant and then decreasing in size to the next largest isotopic variant etc. Alternatively, other combinations may be used to select isotopic varieties of water based on oxygen isotope or, hydrogen isotope differences.

Selection of isotopic varieties of water may also include selection using other physical or magnetic or electrical property differences that could be identified. Such a difference can be used to augment size exclusion or used independently to obtain the desired selection of the isotopic variety or varieties of water.

In one embodiment of the invention isotopes of water are separated by a low energy consuming graphene-based electrochemical pumping method. This may be achieved by roll-to-roll fabrication of membranes that use standard CVD graphene supported on a polymer film such as the commercially available polymer Nafion™. A Nafion™ film was is attached to a carbon cloth. Next, a copper foil with CVD-grown graphene is hot pressed against the Nafion™; and the copper subsequently etched away to release the CVD graphene onto the Nafion™ Electron-beam evaporation is then used to decorate the graphene with Pd nanoparticles that serve as a catalyst to increase the graphene's hydrogen isotope transparency. Finally, the graphene is covered with another carbon cloth, both to prevent accidental damage and also to electrically contact the graphene over the entire area. This fabrication method (as shown in FIG. 3A) may be used to produce graphene-on-Nafion™ membranes of virtually any size.

Reference is now made to FIG. 3B showing the principle of operation of the composite of FIG. 3A in resolving isotopic species by way of an electrochemical pumping system. The two carbon cloths are electrically contacted. In the feed (retentate), a volume of vapor-gas mixtures of $H_2O$—$H_2$ and $D_2O$-$D_2$ with a chosen atomic fraction of protium. The opposite side of the composite faced a vacuum chamber. This setup represents an electrochemical pump in which graphene (a mixed proton-electron conductor) acts as both cathode and semi-permeable membrane to protons and deuterons. One of the carbon cloths is used as the anode and the other to electrically contact the graphene sheet (the system may be operable without the latter cloth). By applying a voltage bias, protons and deuterons are pumped through the Nafion and across the graphene. These isotopes recombine on the permeate side to form $H_2$, $D_2$ and protium deuteride (HD). This principal of electrochemical pumping may be adapted to the resolution of isotopic species as required for any application described herein or similar.

It will be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following are hereby expressly incorporated into this Summary section, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Thus, while there has been described what are believed to be the preferred embodiments of the invention, those skilled in the art will recognize that other and further modifications may be made thereto without departing from the spirit of the invention, and it is intended to claim all such changes and modifications as fall within the scope of the invention. Steps may be added or deleted to methods described within the scope of the present invention.

Although the invention has been described with reference to specific examples, it will be appreciated by those skilled in the art that the invention may be embodied in many other forms.

The present invention will now be more fully described by reference to the following non-limiting preferred embodiments.

EXAMPLES

Commercial evaporators such as the Alfa Laval, consist of smaller effects, or evaporators in series. Juices typically move along one effect and then to the next and the next, until such time that the juice has been concentrated to the desired final brix level. In the process of dehydration, water is removed from each of these effects. In the evaporator mentioned, there are four effects. Effect 1 evaporates the incoming juice firstly and concentrates the juice, before it moves to effect 2, effect 3 and finally effect 4. There can be less or more effects in any given evaporator. Often, juices are concentrated until they reach from between 40 and 70 Brix, depending on the juice processed.

When using commercial evaporators, fractionation involves removal of water from the different effects during juice concentration, a process that produces water with different amounts of heavy or light water ratios or composition (Table 3).

Concentrates vary in brix (One degree Brix is 1 gram of sucrose in 100 grams of solution and represents the strength of the solution as percentage by mass), ranging from 40 (carrots) to 65 and 70 (apple juice, orange juice).

Water extracted as a result of concentrating carrot juice from 10 to 40 brix, using the Alfa Laval series evaporator, produced an aqueous fraction that had a delta-O-18 ratio of between −4.21 and −4.88. This ratio represents the pooling of condensate from all of the 4 in series effects (Sample 1, Table 1). This approach is divergent from prior art methods which teach the production of water from such pooled condensate that is produced by all the effects As an example to demonstrate the process of fractionation of condensate and how it can affect the delta-O-18 ratio, fresh carrot juice was used. This juice was used for:

1. Concentrating carrot juice commercially from 10 Brix to a liquid concentrate with 42 Brix using the Alfa Laval 4 effect in series evaporator (Table 1, Sample 1).
2. Further concentrating, the already, commercial carrot concentrate from 40 brix to 65 brix and collecting the condensate (Table 1, Sample 2).
3. Condensate removed from Effect 1 from Alfa Laval concentrator during carrot concentrate production (Table 1, Sample 4).
4. Condensate removed from Effect 2 from Alfa Laval concentrator during carrot concentrate production (Table 1, Sample 5).
5. Condensate removed from Effect 3 from Alfa Laval concentrator during carrot concentrate production (Table 1, Sample 6).
6. Condensate removed from Effect 4 from Alfa Laval concentrator during carrot concentrate production (Table 1, Sample 7).

This study demonstrated the following:

1. Comparing the delta-O-18 ratio of samples 1 and 2, Table 1, revealed that condensate removed from carrot juice during the process of concentrating from 10 to 40 brix, produced water that had lower heavy water ratios relative to light water. If the 40 Brix concentrate was further dehydrated to 65 brix, using the Buchi Rotavapor R-200 unit, then the condensate became enriched in heavy water, suggesting earlier dehydration preferentially removed the light water.
2. Carrot juice concentration using the Alfa Laval concentrator flows from effect 1 to effect 4 in series and becomes concentrated from 10 to 40 brix. It was shown (Table 3, Samples 4, 5, 6, and 7), that the condensate heavy water content began increasing at each evaporator effect, from order 1 to 4.

In another study, it was found that removing most of the water from sugar cane juice to obtain a molasses, produced a condensate with a Delta O18‰ o VSMOW value of −2.1. Such a value suggests this fraction is very high in heavy water (Table 1, Sample 3). This was carried out to show that if most of the aqueous fraction was removed during evaporation or concentration, rather than just a portion of it, then the condensate would retain the high ratio of heavy water as found in the original sugar cane juice.

To carry out experiments in the laboratory, a Buchi Rotavapor R-200 vacuum, heat distiller (FIG. 1) was used. Briefly, juice volume is aspirated into flask F, through tube A as a result of lower pressure within vessel. The heat bath G was set at around 80 Celsius and the flask F was submerged into the hot water bath so that the juice level was below the water level in the heat bath G. The flask F was continually rotated using an electric motor C, throughout the duration of distillation. Distillate entered the cooling coil B and was condensed using circulating coolant and the distillate was collected in flask E.

TABLE 1

Delta O18 VSMOW of fractionated and non-fractionated carrot juice.

| Sample No. | Water Source | Delta O18‰ VSMOW | comments |
|---|---|---|---|
| 1 | Final condensate removed during commercial carrot juice concentration from 10 brix to 40 brix | −4.47/−4.42/−4.88 | Carrot juice (10 Brix) was commercially concentrated to 40 Brix in the process using an Alfa Laval concentrator. |
| 2 | Condensate from 40 Brix carrot juice concentrate, further evaporated to 65 Brix. | −1.21 | Initially concentrated using Alfa Laval concentrator to 40 Brix. Then this carrot concentrated was further concentrated from 40 brix to 65 brix in a laboratory vacuum distillation Buchi Rotavapor R-200 unit. |
| 3 | Unfractionated condensate removed from sugar cane juice, in the production of Molasses | −2.11 | 90% water removed, molasses remaining. Carried out by ISIS sugar refinery Queensland Australia. |
| 4 | Condensate removed from Effect 1 from Alfa Laval concentrator during carrot concentrate production. | −6.4 | 1 of 4 effects. Effect 1 is first condensate removed from neat carrot juice, during the process of concentrating from 10 to 40 brix. |
| 5 | Condensate removed from Effect 2 from Alfa Laval concentrator during carrot concentrate production. | −6.21 | 2 of 4 effects. Effect 2 is second condensate removed from carrot juice, during the process of concentrating from 10 to 40 brix. |
| 6 | Condensate removed from Effect 3 from Alfa Laval concentrator during carrot concentrate production. | −4.96 | 3 of 4 effects. Effect 3 is third condensate removed from carrot juice, during the process of concentrating from 10 to 40 brix. |
| 7 | Condensate removed from Effect 4 from Alfa Laval concentrator during carrot concentrate production. | −4.12 | 4 of 4 effects. Effect 4 is the last condensate removed from carrot juice, during the process of concentrating from 10 to 40 brix. |

The invention claimed is:

1. A process for preparing a beverage comprising steps of:
obtaining water from plant material;
processing the plant material in a commercial juice producing process into a juice comprising water and solids;
evaporating the juice in an evaporation process;
when the juice has a water content of 30% of less, capturing the evaporated water by a condenser to produce the beverage;
enriching the beverage in at least one of oxygen isotopes;
wherein the at least one of oxygen isotopes is in a range of:
for isotope 16O: 0.99738 to 0.99776 mole fraction;
for isotope 17O: $3.7 \times 10^{-4}$ to $4.0 \times 10^{-4}$ mole fraction; and
for isotope 18O: $1.88 \times 10^{-3}$ to $2.22 \times 10^{-3}$ mole fraction; and
processing the evaporated water with a molecular sieve to remove contaminants.

2. The process of claim 1, wherein the contaminants comprise one or more of ions, proteins, peptides, amino acids, or organic molecules.

3. The process of claim 1, wherein the molecular sieve comprises graphene.

4. The process of claim 1, wherein the molecular sieve comprises a pore size on the order of 9 Angstroms.

5. The process of claim 1, further comprising the step of processing the evaporated water with an activated carbon filter to remove volatile organic compounds.

* * * * *